(12) United States Patent
Lin

(10) Patent No.: US 9,012,332 B2
(45) Date of Patent: Apr. 21, 2015

(54) TEST PIECE AND MANUFACTURING METHOD THEREOF

(71) Applicants: Hui-Ping Chiang, Taoyuan County (TW); Su-Fu Lee, Taoyuan County (TW); Hsiu-Ying Hsu, Taoyuan County (TW)

(72) Inventor: Yu-Lin Lin, Taoyuan County (TW)

(73) Assignees: Hui-Ping Chiang, Taoyuan County (TW); Su-Fu Lee, Taoyuan County (TW); Hsiu-Ying Hsu, Taoyuan County (TW)

(*) Notice: Subject to any disclaimer, the term of this patent is extended or adjusted under 35 U.S.C. 154(b) by 120 days.

(21) Appl. No.: 13/828,695

(22) Filed: Mar. 14, 2013

(65) Prior Publication Data

US 2013/0240255 A1 Sep. 19, 2013

(30) Foreign Application Priority Data

Mar. 15, 2012 (TW) .............................. 101108907 A

(51) Int. Cl.

| | |
|---|---|
| H01L 21/302 | (2006.01) |
| H01L 21/461 | (2006.01) |
| G01N 33/66 | (2006.01) |
| C23F 1/16 | (2006.01) |
| C23F 1/18 | (2006.01) |
| H01L 21/3213 | (2006.01) |
| C23F 1/20 | (2006.01) |
| G01N 33/52 | (2006.01) |
| H05K 1/09 | (2006.01) |
| H05K 1/16 | (2006.01) |
| H05K 3/38 | (2006.01) |

(52) U.S. Cl.
CPC ........ *G01N 33/66* (2013.01); *H05K 1/09* (2013.01); *C23F 1/16* (2013.01); *C23F 1/18* (2013.01); *H01L 21/32134* (2013.01); *C23F 1/20* (2013.01); *H05K 1/16* (2013.01); *H05K 3/388* (2013.01); *H05K 2201/0338* (2013.01); *H05K 2203/1476* (2013.01); *G01N 33/525* (2013.01)

(58) Field of Classification Search
None
See application file for complete search history.

(56) References Cited

U.S. PATENT DOCUMENTS

| | | | |
|---|---|---|---|
| 2008/0206530 A1* | 8/2008 | Song et al. ................ | 428/209 |
| 2008/0268632 A1* | 10/2008 | Luh et al. ................. | 438/612 |

* cited by examiner

*Primary Examiner* — Duy Deo
(74) *Attorney, Agent, or Firm* — Rabin & Berdo, P.C.

(57) ABSTRACT

Disclosed are a test piece and the manufacturing method thereof The test piece includes an insulating substrate and a circuit pattern structure formed on the insulating substrate, wherein circuit pattern structure includes a first metal pattern layer, a second metal pattern layer, a third metal pattern layer, a fourth metal pattern layer, and a fifth metal pattern layer. The first metal pattern layer, the second metal pattern layer, the third metal pattern layer, the fourth metal pattern layer, and the fifth metal pattern layer have same pattern shapes and positions thereof are overlapping in a plane. The first metal pattern layer and the second metal pattern layer are nano-metal films formed by vacuum coating, therefore, the test piece has excellent uniformity of film and low resistance to provide a stable test current to prevent the judging mistakes and to improve the test efficiency.

5 Claims, 8 Drawing Sheets

TEST PIECE AND MANUFACTURING METHOD THEREOF

CROSS-REFERENCES TO RELATED APPLICATIONS

This application claims the priority of Taiwanese patent application No. 101108907, filed on Mar. 15, 2012, which is incorporated herewith by reference.

BACKGROUND OF THE INVENTION

1. Field of the Invention

The present invention generally relates to a test piece, more specifically to a test piece for measuring blood glucose, and the test piece includes at least one nano metal pattern layer.

2. The Prior Arts

Chemical test pieces have already broadly applied in fluidic inspection and testing in decades. Well-known chemical test pieces include a reference electrode and a working electrode, and the manufacturing method and material of electrodes affect the precision of the measuring value. For example, the lower of the resistance of the conductive parts of the chemical test pieces, the better conductive stability is obtained.

Nowadays, the pattern of the reference electrode or the working electrode is pasted on the insulating substrate; however, the adhesive will increase the resistance and decrease the conductivity. The precision of the measuring values would be decreased and the interpretation may be wrong due to those disadvantages. In addition, even there are some manufacturing method uses electroplating to form the pattern on the substrate. However, there are still many processing steps after electroplating, such as etching, so that the electrode pattern is easily peeled. Therefore, a structure and manufacturing method of the test piece to solve the problems is required.

SUMMARY OF THE INVENTION

An objective of the present invention is to provide a test piece including an insulating substrate and a circuit pattern structure formed on the insulating substrate, wherein circuit pattern structure includes a first metal pattern layer, a second metal pattern layer, a third metal pattern layer, a fourth metal pattern layer, and a fifth metal pattern layer laminated from bottom to up in sequence. The first metal pattern layer, the second metal pattern layer, the third metal pattern layer, the fourth metal pattern layer, and the fifth metal pattern layer have same pattern shapes, and positions thereof are overlapping in a plane. The thickness of the first metal pattern layer is 20~50 nm, and the first metal pattern layer is formed of at least one of Cr, Ni, Ti, Al, Sn, In, Pd, W, Fe, Au, Ag, Pt, and steel. The thickness of the second metal pattern layer is 40~90 nm, and the second metal pattern layer is formed of at least one of Cu, Ni, Ti, Al, Sn, In, Pd, W, Fe, Au, Ag, Pt and steel.

Another objective of the present invention is to provide a manufacturing method of the test piece including a first vacuum coating step, a second vacuum coating step, a photolithography step, a first etching step, a second etching step, a photoresist removing step, and a chemical build-up step. The first vacuum coating step is forming a first metal film on the insulating substrate by evaporation, sputtering, or atomic layer deposition (ALD). The second vacuum coating step is forming a second metal film on the first metal film by evaporation, sputtering, or ALD. The photolithography step is forming a photoresist pattern layer on the second metal film. The first etching step is removing parts of the second metal film which is uncovered by the photoresist pattern layer by using a first etchant to form the second metal pattern layer. The second etching steps is removing parts of the first metal film which is uncovered by the photoresist pattern layer and the second metal pattern layer by using a second etchant to form the first metal pattern layer. The photoresist removing step is removing the photoresist pattern layer. The chemical build-up step is forming the third metal pattern layer, the fourth metal pattern layer, and the fifth metal pattern layer on the second metal pattern layer in sequence by electroplating or electroless plating. The first etchant is not reacting to the first metal film, and the second etchant is not reacting to the second metal pattern layer.

The technical characteristics of the present invention are that forming the first metal pattern layer and the second metal pattern layer by vacuum coating, therefore, the excellent uniformity of film is obtained, for example, the average error is less than 300Å. In addition, the test piece has low resistance, so as to provide a stable test current to prevent the interpretation mistakes and to improve the test efficiency.

BRIEF DESCRIPTION OF THE DRAWINGS

The present invention can be understood in more detail by reading the subsequent detailed description in conjunction with the examples and references made to the accompanying drawings, wherein.

DETAILED DESCRIPTION OF THE PREFERRED EMBODIMENT

The present invention may be embodied in various forms and the details of the preferred embodiments of the present invention will be described in the subsequent content with reference to the accompanying drawings. Modifications of the shape of the present invention shall too be considered to be within the spirit of the present invention.

Figure 1:
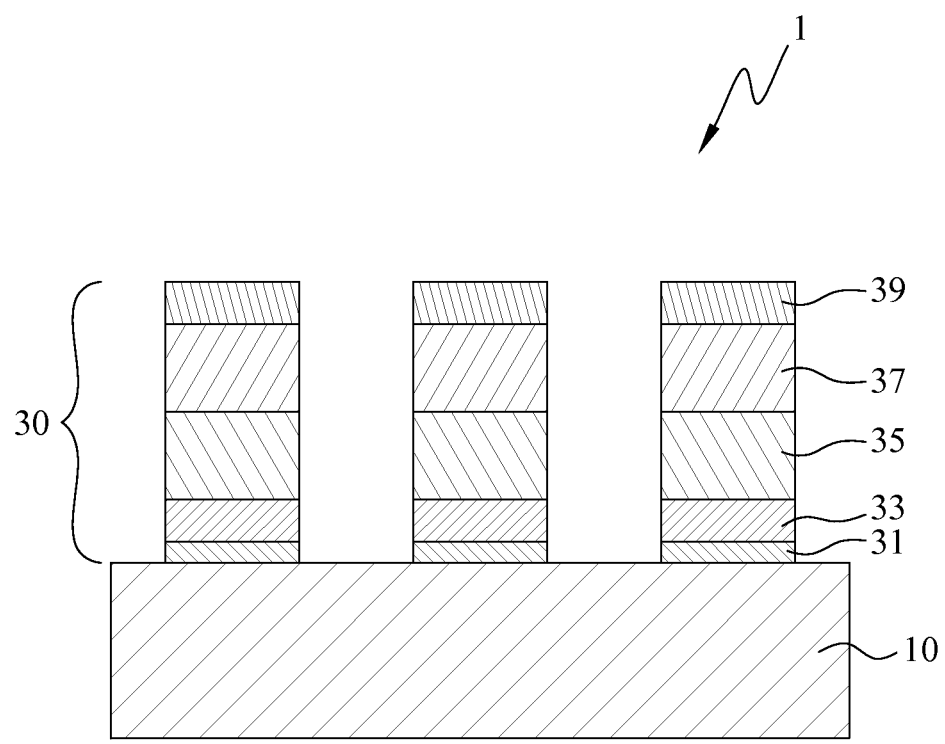
FIG. 1 is a schematic drawing for illustrating a test piece of the present invention.

FIG. 1 is a schematic drawing for illustrating a test piece of the present invention. As shown in FIG. 1, the test piece 1 of the present invention includes to an insulating substrate 10, and a circuit pattern structure 30 formed on the insulating substrate 10, wherein circuit pattern structure 30 includes a first metal pattern layer 31, a second metal pattern layer 33, a third metal pattern layer 35, a fourth metal pattern layer 37, and a fifth metal pattern layer 39 laminated from bottom to up in sequence. The first metal pattern layer 31, the second metal pattern layer 33, the third metal pattern layer 35, the fourth metal pattern layer 37, and the fifth metal pattern layer 39 have same pattern shapes, and positions thereof are overlapping in a plane.

The insulating substrate 10 is formed of polyethylene terephthalate (PETE), high-density polyethylene (HDPE), polypropylene (PP), polymind (PI); and the thickness of the insulating substrate 10 is 25~500 μm.

The thickness of the first metal pattern layer 31 is 20~50 nm, and the first metal pattern layer 31 is formed of at least one of Cr, Ni, Ti, Al, Sn, In, Pd, W, Fe, Au, Ag, Pt, and steel, wherein Cr is preferred. The thickness of the second metal pattern layer 33 is 40~90 nm, and the second metal pattern layer 33 is formed of at least one of Cu, Ni, Ti, Al, Sn, In, Pd, W, Fe, Au, Ag, Pt and steel, wherein Cu is preferred. The thickness of the third pattern layer 35 is 20~30 μm, and the third metal pattern layer 35 is formed of Pd. The thickness of the fourth metal pattern layer 37 is 20~30 μm, and the fourth metal pattern layer 37 is formed of Ni. The thickness of the fifth metal pattern layer 39 is 2~5 nm, and the fifth metal pattern layer 39 is formed of at least one of Au, Ag, Cu, Ni, Ti, Pd, wherein Au is preferred.

Figure 2:
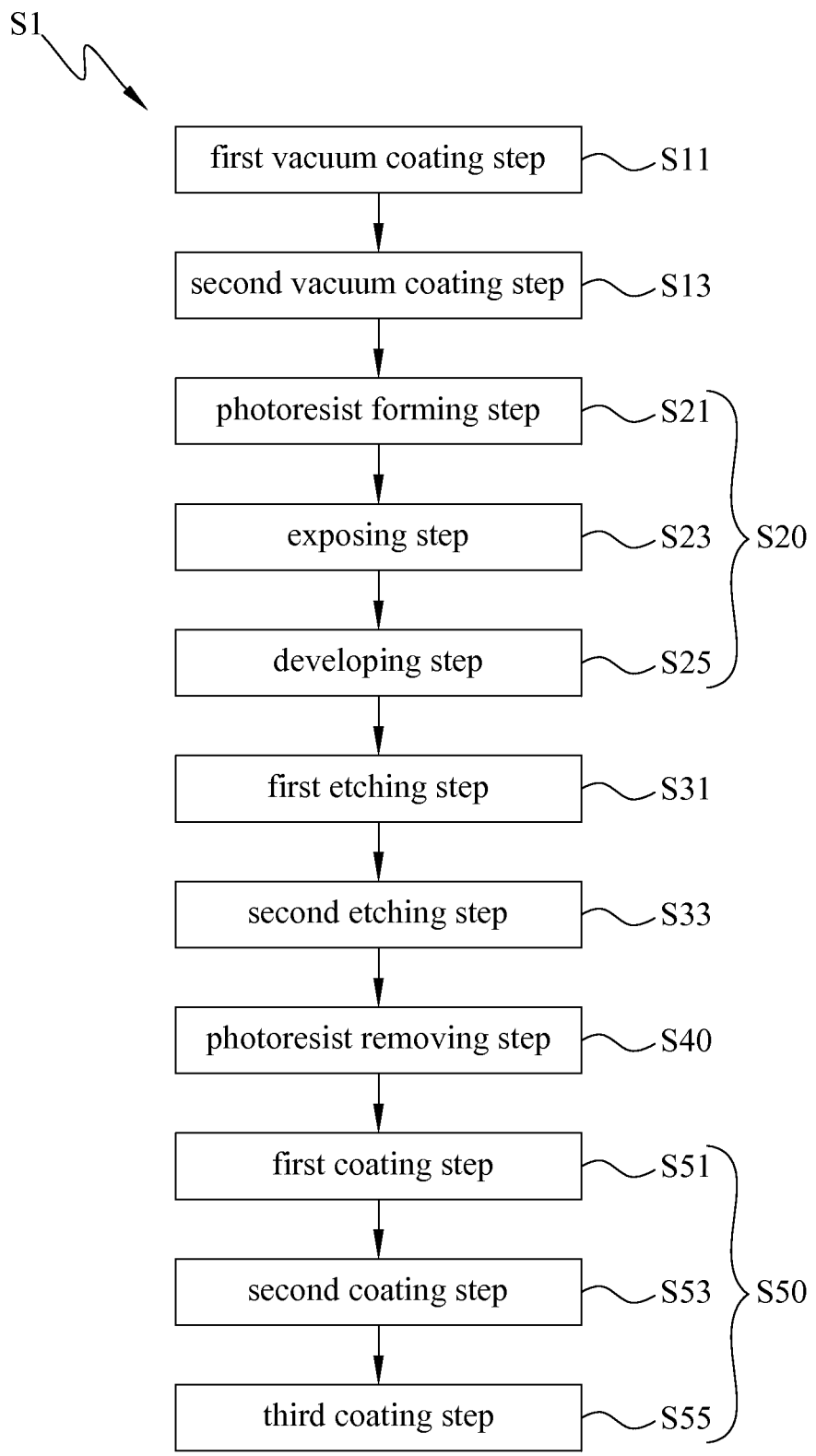
FIG. 2 is the flow chart of the manufacturing method of the test piece of the present invention.
Figure 3A:
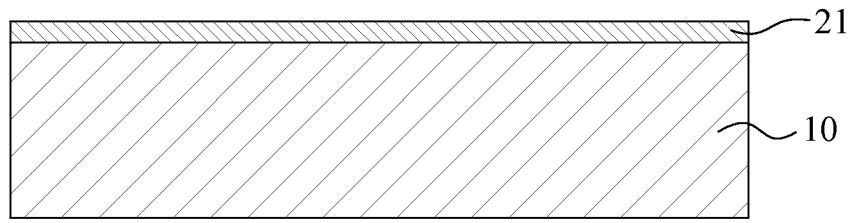
FIGS. 3A to 3K are the cross section schematic drawings step by step of the manufacturing method of the test piece of the present invention.
Figure 3B:
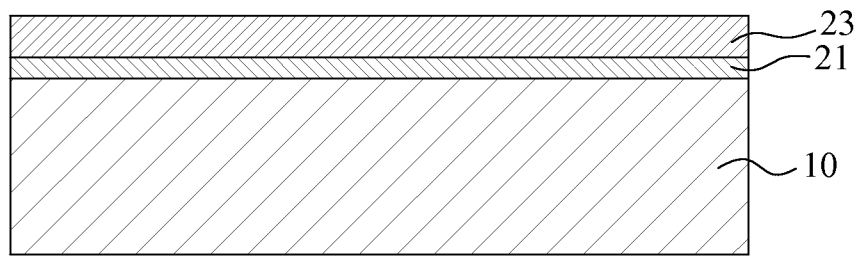

FIG. 2 and FIGS. 3A to 3K are the flow chart of the manufacturing method of the test piece of the present invention and cross section schematic drawings step by step. As shown in FIG. 2, the manufacturing method of the test piece Si of the present invention includes a first vacuum coating step S11, a second vacuum coating step S13, a photolithography step S20, a first etching step S31, a second etching step S33, a photoresist removing step S40, and a chemical build-up step S50. With reference to FIGS. 3A and 3B, the first vacuum coating step S11 is forming a first metal film 21 on the insulating substrate 10 by evaporation, sputtering, or atomic layer deposition (ALD). The second vacuum coating step S13 is forming a second metal film 23 on the first metal film 21 by evaporation, sputtering, or ALD.

Figure 3C:
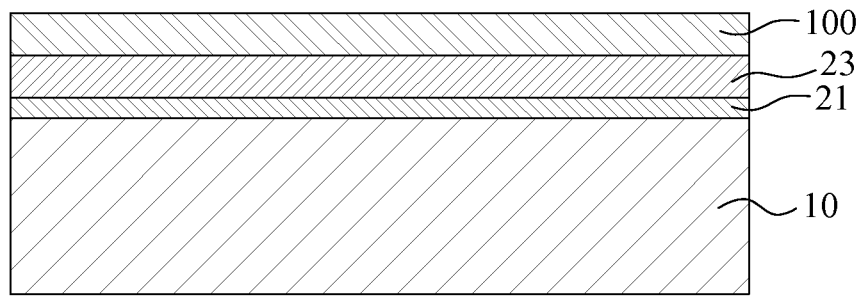
Figure 3D:
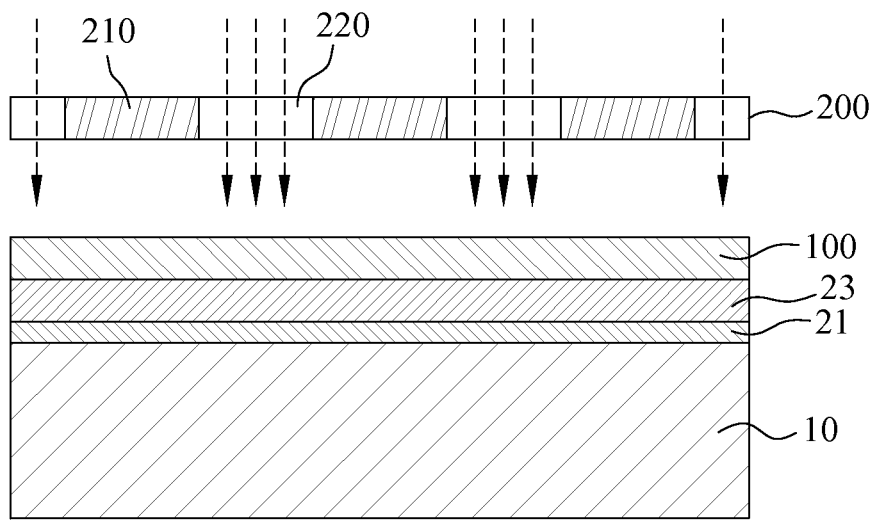
Figure 3E:
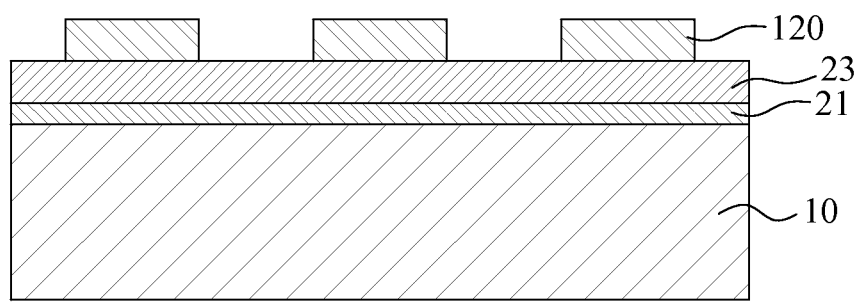

With reference FIG. 2 and FIGS. 3C and 3E, the photolithography step S20 includes a photoresist forming step S21, an exposing step S23, and a developing step S25. As shown in FIG. 3C, the photoresist forming step S21 is forming a photoresist layer 100 on the second metal film 23. As shown in FIG. 3D, the exposing step S23 is performing light exposure on the photoresist layer 100 with a photomask 200. The developing step S25 is rinsing the exposed photoresist layer 100 with a developer to form a photoresist pattern layer 120 as shown in FIG. 3E. The example described in the embodiment of FIG. 3E is using positive photoresist, such that the portion of photoresist layer 100 corresponding to the light-transmitting portion 210 of the photomask 200 is dissolved by the developer, and the portion of photoresist layer 100 corresponding to the light-blocking portion 210 of the photomask is are not dissolved by the developer and remained after rinsing. The positive photoresist is only an example for describing; the negative photoresist can be used according to the actual condition.

Figure 3F:
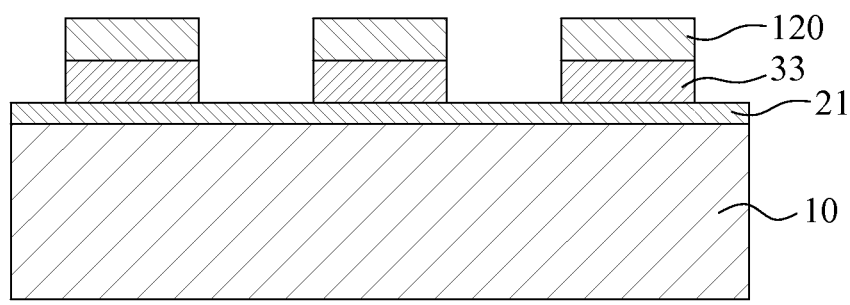

With reference to FIG. 3F, the first etching steps S31 is removing parts of the second metal film 23 which is uncovered by the photoresist pattern layer 120 by using a first etchant, such that the second metal pattern layer 33 is formed. The first etchant is not reacting to the first metal film 21. The first etchant includes a acid solution and an oxidizing agent, wherein the acid solution includes at least one of phosphoric acid, oxalic acid, sulfur acid, hydrochloric acid, acetic acid and lactic acid, and the oxidizing agent includes at least one sodium persulfate (SPS), hydrogen peroxide, ammonium persulfate and ozone.

Figure 3G:
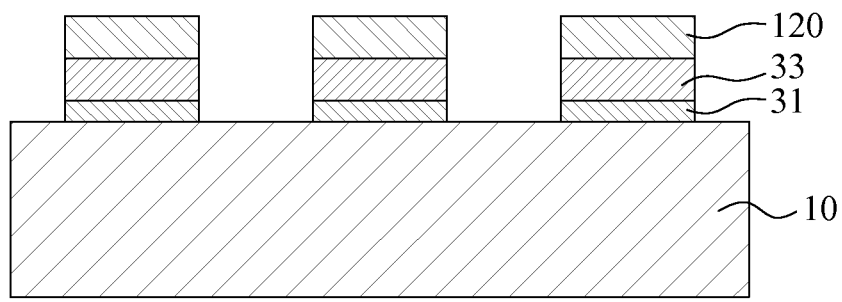

With reference to FIG. 3G, the second etching steps S33 is removing parts of the first metal film 21 which is uncovered by the photoresist pattern layer 120 and the second metal pattern layer 33 by using a second etchant, such that the first metal pattern layer 31 is formed. The second etchant is not reacting to the second metal pattern layer 33. The second etchant includes a alkaline solution, a second oxidizing agent and a salt, wherein the alkaline solution includes at least one of sodium hydroxide, potassium hydroxide, monoethanolamine (MEA), and triethylamine (TEA), the second oxidizing agent includes at least one potassium permanganate ($KMnO_4$), potassium dichromate ($K_2Cr_2O_7$), sodium dichromate ($Na_2Cr_2O_7$), ammonia cerium nitrate (($NH_4)_2Ce(NO_3)_6$), and the salt includes at least one of sodium phosphate ($Na_3PO_4$), sodium dihydrogen phosphate ($NaH_2PO_4$), disodium hydrogen phosphate ($Na_2HPO_4$), sodium carbonate ($Na_2CO_3$), sodium hydrogen carbonate ($NaHCO_3$), and sodium oxalate ($Na_2C_2O_4$).

Figure 3H:
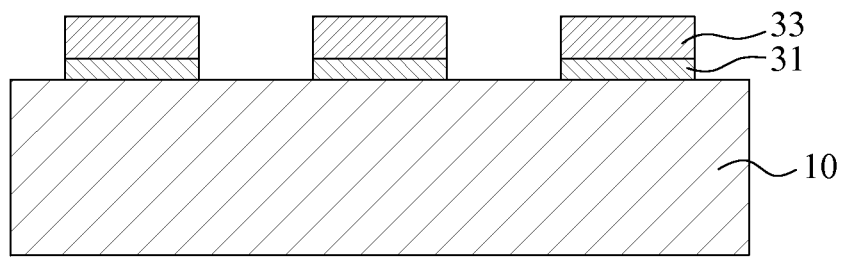
Figure 3I:
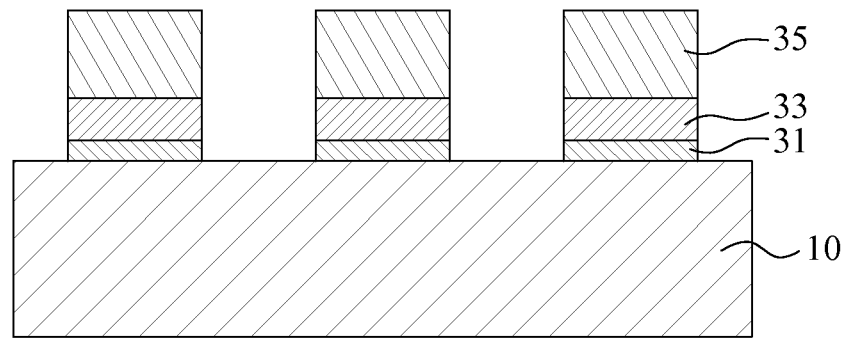
Figure 3J:
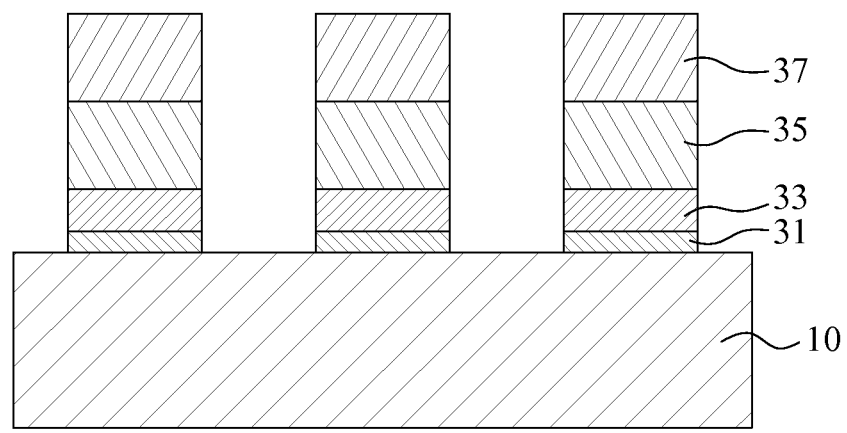

With reference to FIG. 3H, the photoresist removing step S40 is removing the photoresist pattern layer 120 by organic solvent. Moreover, further immersing the structure shown in FIG. 3G in a neutralizing agent between the second etching steps S33 and the photoresist removing step S40, wherein the neutralizing agent includes a third oxidizing agent and a reducing agent. The third oxidizing agent includes at least one of sulfur acid, oxalic acid, lactic acid and hydrogen peroxide; and the reducing agent includes hydrazine, tetramethylammonium hydroxide (TMAH), dimethyl sulfoxide (DMSO), and tetrahydrofuran (THF).

Figure 3K:
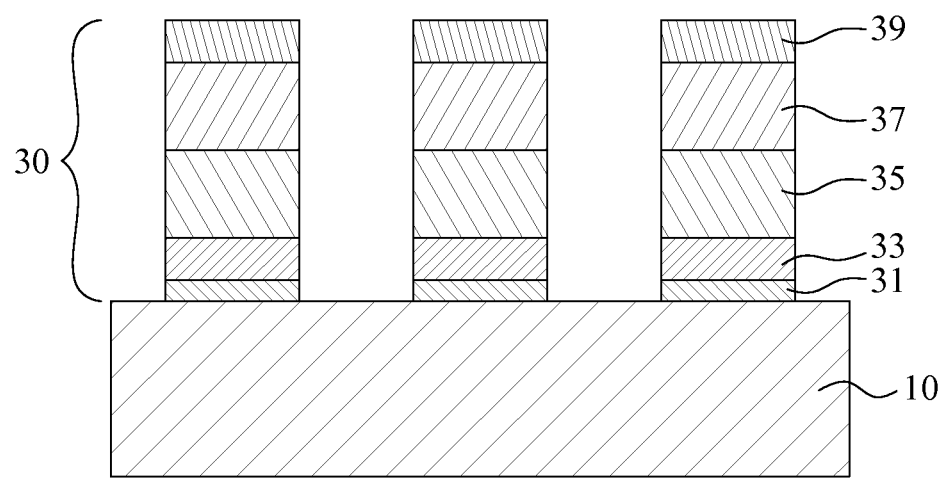

The chemical build-up step S50 includes a first coating step S51, a second coating step S53, and a third coating step S55. As shown in FIGS. 31 to 3K, the first coating step S51, the second coating step S53, and the third coating step S55 are forming the third metal pattern layer 35, the fourth metal pattern layer 37, and the fifth metal pattern layer 39 on the second metal pattern layer 33 in sequence by electroplating or electroless plating (chemical plating).

The technical characteristics of the present invention are that forming the first metal pattern layer 31 and the second metal pattern layer 33 by vacuum coating, therefore, the excellent uniformity of film is obtained, for example, the average error is less than 300Å. In addition, the test piece has low resistance, so as to provide a stable test current to prevent the interpretation mistakes and to improve the test efficiency.

Although the present invention has been described with reference to the preferred embodiments, it will be understood that the invention is not limited to the details described thereof Various substitutions and modifications have been suggested in the foregoing description, and others will occur to those of ordinary skill in the art. Therefore, all such substitutions and modifications are intended to be embraced within the scope of the invention as defined in the appended claims.

What is claimed is:

1. A manufacturing method of a test piece, comprising:
a first vacuum coating step for firming a first metal film on an insulating substrate by evaporation, sputtering, or atomic layer deposition (ALD);
a second vacuum coating step for forming a second metal film on the first metal film by evaporation, sputtering, or ALD;
a photolithography step for forming a photoresist pattern layer on the second metal film;
a first etching step for removing parts of the second metal film which are uncovered by the photoresist pattern layer by using a first etchant to form a second metal pattern layer;
a second etching step for removing parts of the first metal film which are uncovered by the photoresist pattern layer and the second metal pattern layer by using a second etchant to form a first metal pattern layer;
after said second etching step, immersing the structure with the first metal pattern layer, the second metal pattern layer and the photoresist pattern layer on the insulating substrate in a neutralizing agent, wherein the neutralizing agent includes a third oxidizing agent including at least one of sulfur acid, oxalic acid, lactic acid and hydrogen peroxide, and a reducing agent including hydrazine, tetramethylammonium hydroxide (TMAH), dimethyl sulfoxide (DMSO), and tetrahydrofuran (THF);

a photoresist removing step, performed after said immersing, for removing the photoresist pattern layer; and a chemical build-up step for forming a third metal pattern layer, a fourth metal pattern layer, and a fifth metal pattern layer on the second metal pattern layer in sequence by electroplating or electroless plating, wherein the first metal pattern layer, the second metal pattern layer, the third metal pattern layer, the fourth metal pattern layer, and the fifth metal pattern layer have same pattern shapes and positions thereof overlap in a plane, the first etchant does not react to the first metal film, and the second etchant does not react to the second metal pattern layer.

2. The manufacturing method as claimed in claim 1, wherein the thickness of the first metal pattern layer is 20~50 nm, the first metal pattern layer is formed of at least one of Cr, Ni, Ti, Al, Sn, In, Pd, W, Fe, Au, Ag, Pt, and steel, the thickness of the second metal pattern layer is 40~90 nm, and the second metal pattern layer is formed of at least one of Cu, Ni, Ti, Al, Sn, In, Pd, W, Fe, Au, Ag, Pt and steel.

3. The manufacturing method as claimed in claim 1, wherein the photolithography step includes a photoresist forming step, an exposing step, and a developing step, wherein the photoresist forming step forms a photoresist layer on the second metal film, the exposing step performs light exposure on the photoresist layer with a photomask, and the developing step rinses the exposed photoresist layer with a developer to form the photoresist pattern layer.

4. The manufacturing method as claimed in claim 1, wherein the first etchant includes an acid solution including at least one of phosphoric acid, oxalic acid, sulfur acid, hydrochloric acid, acetic acid and lactic acid, and an oxidizing agent including at least one sodium persulfate (SPS), hydrogen peroxide, ammonium persulfate and ozone; the second etchant includes a alkaline solution including at least one of sodium hydroxide, potassium hydroxide, monoethanolamine (MEA), and triethylamine (TEA), a second oxidizing agent including at least one potassium permanganate ($KMnO_4$), potassium dichromate ($K_2Cr_2O_7$), sodium dichromate ($Na_2Cr_2O_7$), ammonia cerium nitrate (($NH_4$)$_2Ce(NO_3)_6$), and a salt including at least one of sodium phosphate ($Na_3PO_4$), sodium dihydrogen phosphate ($NaH_2PO_4$), &sodium hydrogen phosphate ($Na_2HPO_4$), sodium carbonate ($Na_2CO_3$), sodium hydrogen carbonate ($NaHCO_3$), and sodium oxalate ($Na_2C_2O_4$).

5. The manufacturing method as claimed in claim 1, wherein the thickness of the third metal pattern layer is 20~30 μm, the third metal pattern layer is formed of Pd, the thickness of the fourth metal pattern layer is 20~30 μm, the fourth metal pattern layer is formed of Ni, the thickness of the fifth metal pattern layer is 2~5 μm, and the fifth metal pattern layer is formed of at least one of Au, Ag, Cu, Ni, Ti, and Pd.

* * * * *